United States Patent [19]

Sato et al.

[11] Patent Number: 5,063,936
[45] Date of Patent: Nov. 12, 1991

[54] INTERNAL PRESSURE MEASURING DEVICE USING CATHETER WITH MULTIPLE LUMENS

[75] Inventors: Masamitu Sato, Akita; Masami Tanishima, Tokyo, both of Japan

[73] Assignee: Nihon Kohden Corporation, Tokyo, Japan

[21] Appl. No.: 498,070

[22] Filed: Mar. 23, 1990

[51] Int. Cl.⁵ .............................................. A61B 5/02
[52] U.S. Cl. ................................... 128/674; 128/692; 128/650; 128/748; 73/4 R
[58] Field of Search ............... 128/672, 673, 674, 675, 128/691, 692, 645, 650, 656–658, 748, 637; 73/4 R, 64.3, 708

[56] References Cited

U.S. PATENT DOCUMENTS

| | | | |
|---|---|---|---|
| 4,603,699 | 8/1986 | Himpens | 128/673 |
| 4,779,626 | 10/1988 | Peel et al. | 128/675 |
| 4,807,477 | 2/1989 | Myers et al. | 73/708 |
| 4,854,326 | 8/1989 | Merrick | 128/675 |

Primary Examiner—Stephen C. Pellegrino
Assistant Examiner—Robin R. Longo
Attorney, Agent, or Firm—Sughrue, Mion, Zinn, Macpeak & Seas

[57] ABSTRACT

Pressure measuring lumen allows a coarse pressure value of a subject to be read. A liquid filled lumen is allowed to pressure communicate with an atmosphere adjacent to a patient, through the use of a membrane and an atomosphere-opening lumen. A liquid pressure value read from the liquid filled lumen is used to adjust the pressure value to compensate for pressure changes induced by a positional change of the subject.

8 Claims, 2 Drawing Sheets

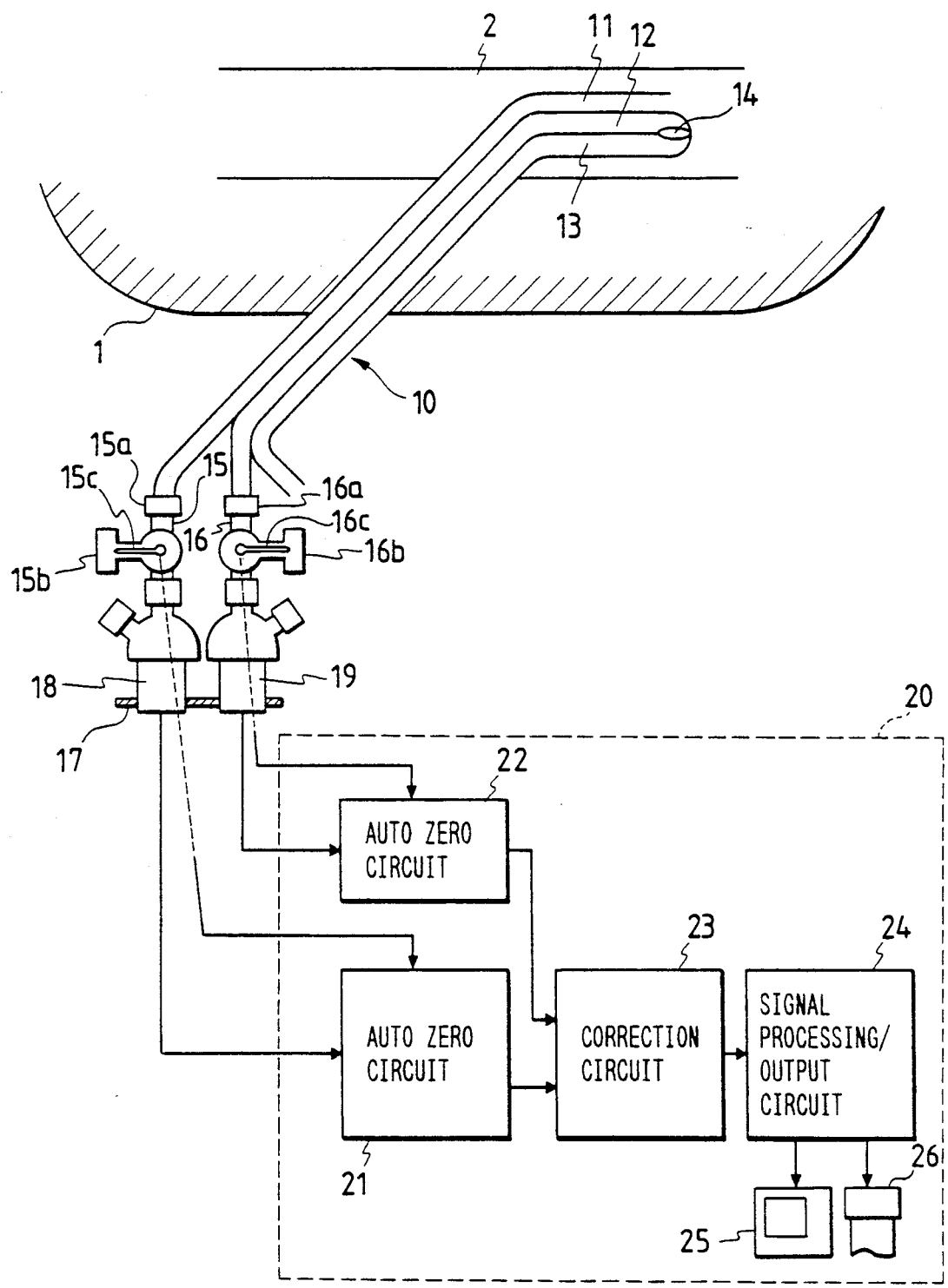

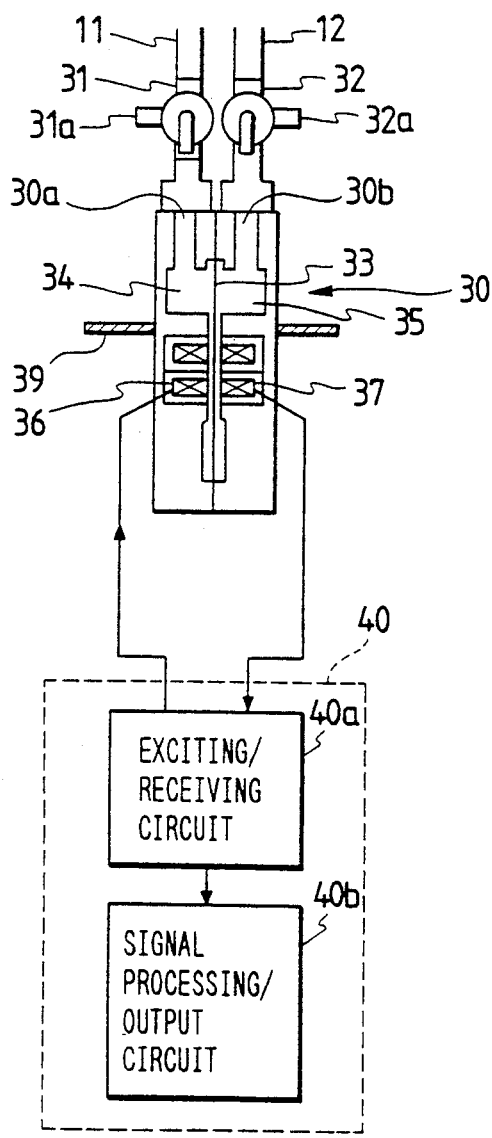
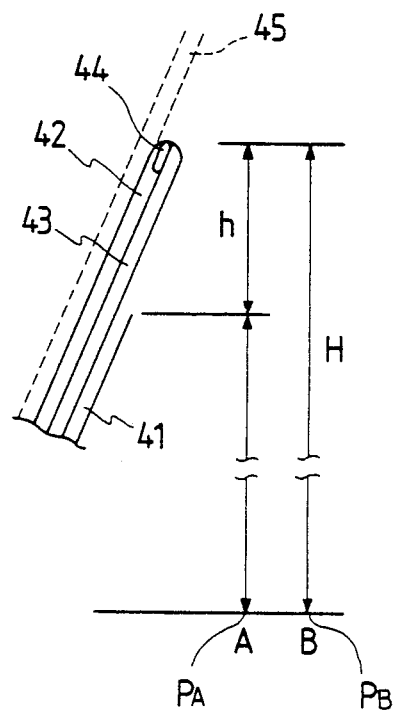

INTERNAL PRESSURE MEASURING DEVICE USING CATHETER WITH MULTIPLE LUMENS

BACKGROUND OF THE INVENTION

This invention relates to a device for measuring an internal pressure in a living body or organism by inserting a catheter into the living body.

Such an internal pressure measuring method has heretofore been extensively used for clinical or other purposes, for example, in an invasive blood pressure monitoring system.

In most of the conventional devices, a pressure transducer (pressure-electric signal transducer) is disposed externally of the living body, and the internal pressure in the living body is fed to the transducer via a catheter introduced into the living body, thereby effecting the measurement. In this method, an atmosphere-opening point of the pressure measuring transducer is set at the same level or height as a pressure reference point (for example, the heart (at the point of tricuspid valve) when measuring the blood pressure) of the object to be measured, and the pressure-receiving surface of the transducer is caused to be open to the atmosphere to thereby effect a zero point adjustment, and thereafter the pressure measurement is carried out. However, this method has a vital drawback. More specifically, when the position of the object to be measured with respect to the transducer is varied, the hydrostatic pressure (plus or minus) of the liquid in the catheter is added, and this causes an error in measurement value. Particularly when measuring a pressure usually of several mmHg such as the central venous pressure, a position variation of 1 cm causes an error (variation) of 0.73 mmHg. This error can not be ignored. For this reason, from a clinical point of view, it has been difficult to effect a significant measurement without re-adjusting the position of the transducer, and it has been still more difficult to effect the monitoring for a long period of time in a stable manner.

In conventional devices of another type under consideration, a transducer is mounted on the distal end of a catheter. Such a device obviates the need for the re-adjustment of the position of the transducer necessitated by the position variation; however, the zero point adjustment of the transducer can be made only before the catheter is introduced into the living body, and once the catheter is introduced into the living body, the zero point adjustment can not be made in the body. Thus, such conventional device is also not suited for a reliable, long-term monitoring.

SUMMARY OF THE INVENTION

It is therefore an object of this invention to provide an internal pressure measuring device which can easily effect a zero point adjustment with a catheter kept introduced in the living body, and is not influenced by a variation in relative position between an object to be measured and a transducer.

The above object of the invention is achieved by a device having the following features:

(1) A catheter for measuring an internal pressure in a living body has at least three lumens. The first lumen has an open distal end, and is used as a pressure measuring lumen. The second lumen has a closed distal end, and is filled with a liquid, and is used as a height-correcting liquid filling lumen. The third lumen has a closed distal end, and allows the air thereinto, and is used as a height-correcting atmosphere-opening lumen. Additional lumen or lumens may be provided for other purposes.

(2) The height-correcting liquid filling lumen and the height-correcting atmosphere-opening lumen are separated from each other by a partition wall, and a membrane is provided at that portion of this partition wall disposed at the position of a pressure reference point for the internal pressure measurement. The membrane is impermeable to the liquid and is permeable to the air.

(3) The proximal end of the pressure measuring lumen is connected via a three-way cock to an inlet of a pressure-measuring pressure transducer (or corresponding pressure differential transducer). Similarly, the proximal end of the height-correcting liquid filling lumen is connected to an inlet of a height-correcting pressure transducer (or corresponding pressure differential transducer). The proximal end of the height-correcting atmosphere-opening lumen is open to the atmosphere.

(4) When the two pressure transducers are to be used, the two transducers are mounted on a common flat surface of a base, and a circuitry is connected to the transducers so that the electric output of the pressure-measuring pressure transducer can be corrected by the electric output (which represents the head value reflecting the hydrostatic pressure corresponding to the height of the membrane) of the height-correcting pressure transducer. The output of this circuitry is connected to a display circuit or a recording circuit.

(5) In the case where the corresponding pressure differential transducer is used in combination with the catheter of the present invention, this transducer is mounted on a base, and the output of the transducer is connected to a display circuit or a recording circuit.

For effecting the measurement, the same liquid as a sterilized liquid filled in the pressure measuring lumen is fed from the three-way cock, connected to the proximal end of the height-correcting liquid filling lumen of the internal pressure measuring catheter, to the height-correcting liquid filling lumen and is filled therein. The catheter is introduced into the living body in an ordinary manner in such a manner that the membrane portion is disposed at a desired pressure reference point. As a result, the height-correcting liquid filling lumen is exposed at its membrane portion to the atmosphere through the membrane, and applies to the height-correcting pressure transducer a pressure corresponding to the head with respect to the pressure-measuring pressure transducer. With this arrangement, even when the position of the pressure reference point of the living body relative to the transducers disposed externally of the living body is varied, the head value corresponding to the height variation can be obtained. By virtue of this value, when the exclusive height-correcting pressure transducer is connected, an error due to a variation in the relative position between the object to be measured and the transducer can be corrected in terms of the circuitry. Also, when the differential pressure transducer is connected, such error can be corrected at the pressure stage prior to the pressure-electric signal transducing.

BRIEF DESCRIPTION OF THE DRAWINGS

FIG. 1 shows a cross-section of a catheter and associated circuitry of a pressure measuring device according to one preferred embodiment of the invention;

FIG. 2 shows a cross-section of a catheter and associated circuitry of a pressure measuring device according to another embodiment of the invention; and FIG. 3 is a schematic cross-sectional view of an important portion of a catheter of a pressure measuring device according to a further embodiment of the invention.

DETAILED DESCRIPTION OF THE PREFERRED EMBODIMENTS

FIG. 1 shows a preferred embodiment of a pressure measuring device of the present invention.

In FIG. 1, reference numeral 10 denotes a pressure measuring catheter which has an ordinary diameter and is flexible and straight. The catheter 10 comprises a pressure measuring lumen 11 having an open distal end, a liquid fill lumen 12 which has a closed distal end disposed flush with the distal end of the lumen 11 and being filled, for example, with physiological saline, and an atmosphere-opening lumen 13 which has a water repellent membrane 14 disposed at its surface in contact with the distal end of the lumen 12 and made, for example, of Goretex (registered trademark) or a membrane filter. The membrane 14 is impermeable to physiological saline and is permeable to the air. The lumen 13 has a closed distal end which is also disposed flush with the distal end of the lumen 12, and the proximal end portion of the lumen 13 is bent laterally with respect to a main portion of the catheter 10 and is open to the atmosphere.

The proximal end of the pressure measuring lumen 11 is connected to a pressure transducer 18 via one inlet 15a of a three-way cock 15. The liquid fill lumen 12 is connected to a height-correcting pressure transducer 19 via one inlet 16a of a three-way cock 16. These transducers 18 and 19 are mounted on a common base 17 which is either position-adjustable in a vertical direction or is fixed.

A pressure measuring circuit portion 20 with a height-correcting circuit is connected to the proximal ends of the transducers 18 and 19. This circuit portion comprises: auto zero circuits 21 and 22 which open the pressure receiving surfaces of these transducers to the atmosphere via another inlet 15c and 16c of the three-way cocks 15 and 16 when levers 15c and 16c of the three-way cocks 15 and 16 are manually operated, and automatically effect automatic equilibrium operations based on values of the pressure-electric signal when an auto zero switch is operated; a correction circuit for subtracting the output signal of the auto zeros circuit 22 (which has a polarity of plus or minus) from the output signal of the auto zero circuit 21 obtained at the time of the measurement; and a signal processing/output circuit 24 which processes the height-corrected pressure signal, and causes it to be displayed on a Braun tube 25, and causes it to be recorded in a recorder 26.

The operation of the pressure measuring device thus constructed is as follows:

The pressure measuring catheter 10 is inserted into a desired pressure measuring point in an ordinary manner in such a manner that the membrane is disposed at the pressure reference point (at the point of tricuspid valve) of the body 1. The proximal end of the atmosphere-opening lumen 13 is extended from the body 1 and is open to the atmosphere. The distal end of the catheter is disposed at the highest position in order to positively supply the liquid into the height-correcting liquid filling lumen, and the liquid is gently supplied into this lumen without introducing bubbles thereinto until the liquid can be no longer supplied. Thereafter, the membrane portion of the catheter is disposed at the same level or height as the three-way cock, and the three-way cock is once caused to be open to the atmosphere, and then the three-way cock is rotated so as to connect the transducer to the height-correcting liquid filling lumen. The inlets 15b and 16b are maintained at the same height by means of the base 17. By operating the levers 15c and 16c, the pressure receiving surfaces of the transducers 18 and 19 are caused to be temporarily opened to the atmosphere via the respective inlets 15b and 16b, and the auto zero circuits 21 and 22 are caused to effect automatic equilibrium operations through the operation of a switch.

Then, by returning the levers 15c and 16c to their original positions, the pressure measurement is started. In this condition, when the base 17 is disposed at a level lower than the body 1, the transducer 19 receives a pressure corresponding to the liquid disposed between the distal end of the pressure measuring catheter 10 and the inlet 15b for the transducer 18, so that the auto zero circuit 22 outputs a plus correction signal of the corresponding level. On the other hand, the pressure signal which is detected and transduced to pressure-electric signal by the transducer 18 and is produced in the auto zero circuit 21 is subtracted in the correction circuit 23, so that the actual signal reduced in level is loaded into the signal processing/output circuit 24. As a result, the corrected pressure data are displayed on the Braun tube 25 and are also recorded in the recorder 26.

During the above operation, when the body position is varied so that the catheter 10 is varied from the initial position, the liquid fill lumen 12 is moved in response to this variation, so that the transducer 19 receives a pressure variation corresponding to this catheter position variation to thereby effect the correction. As a result, highly precise pressure data which are not influenced by the variation of the body position are monitored.

In this case where the base 17 is adjusted to the pressure reference point of the body, and then the inlets 15b and 16b are disposed above the pressure reference point as a result of a variation of the body position, the auto zero circuit 22 outputs a minus correction signal of a corresponding level, and this correction signal is subtracted from the actual pressure signal in the correction circuit 23 to increase its level.

FIG. 2 shows another embodiment in which the height correcting means does not include the circuit portion.

In this case, instead of the transducers for exclusive use, a differential pressure transducer 30 is connected to the proximal ends of the pressure measuring lumen 11 and liquid fill lumen 12 of FIG. 1. More specifically, this differential pressure transducer is mounted on a base 39, and has a pressure receiving chamber 34 communicating with the pressure measuring lumen 11 via a three-way cock 31 and an inlet 30a, and a pressure receiving chamber 35 disposed in juxtaposed relation to the pressure receiving chamber 34 and communicating with the liquid fill lumen 12 via a three-way cock 32 and an inlet 30b. The two pressure receiving chambers are separated from each other by a diaphragm 33 of a magnetic material extending downwardly. The differential pressure transducer also includes coils 36 and 37 which constitute a bridge circuit for detecting a displacement diaphragm. A pressure measuring circuit portion 40 comprises an exciting/receiving circuit 40a for effecting a zero adjustment and temperature compensation of the bridge, and a signal processing/output circuit 40b which detects the pressure value from the output signal of the exciting/receiving circuit to cause it to be displayed or recorded.

For effecting the measurement, by operating levers of the three-way cocks 31 and 32, the pressure receiving chambers 34 and 35 are caused to be temporarily opened to the atmosphere via inlets 31a and 32a. In this condition, the pressure value signal output from the exciting/receiving circuit 40a is set to zero. Then, the levers are returned to the original positions, and the measurement is started. The pressure receiving chamber 34 receives a pressure corresponding to the pressure to be measured, whereas the pressure receiving chamber 35 receives a pressure corresponding to the liquid (pointed at a same height or level) of the liquid fill lumen 12, and this amount is subtracted from the value of the pressure received by the pressure receiving chamber 34. When the body position is varied upwardly, the diaphragm 33 is displaced in such a manner that a pressure variation received by the pressure receiving chamber 35 is subtracted from the pressure received by the pressure receiving chamber 34. When the body position is varied downwardly, the value of the pressure received by the pressure receiving chamber 34 is added to the pressure received by the pressure receiving chamber 34. Therefore, the exciting/receiving circuit 40a outputs a height-corrected pressure signal, and the signal processing/output circuit 40b outputs a monitoring signal.

FIG. 3 shows a further embodiment employing a thermodilution pulmonary artery catheter in which a blood pressure measuring lumen 41 is disposed rearwardly from the position of the pressure reference point so as to correspond to a central venous pressure measuring position. A liquid fill lumen 42 with a membrane 44 as well as an atmosphere-opening lumen 43 is formed in such a position as to be maintained at the pressure reference point. These lumens 41 and 42 are connected at their proximal ends to the pressure transducers as described in FIGS. 1 and 2. In this case, when the distal end of the liquid fill lumen 42 is disposed near the reference height, that is, valva tricuspidalis, the measurement can be carried out regardless of a variation of the body position even if the blood pressure measuring lumen 41 is displaced from the reference height, because of the relation mentioned below and the relation shown in FIG. 3. More specifically, if P represents the absolute pressure of the pump system disposed at the reference height, $P_H$ represents a pressure due to the reference height H, $P_h$ represents a hydrostatic pressure corresponding to the displacement height h, $P_A$ represents a pressure at a measuring point A of the blood pressure measuring lumen 41, and $P_B$ represents a pressure at a measuring point B of the liquid fill lumen 42, then the following relation is established:

$$P_A = (P + P_h) + (P_H - P_h) = P + P_H$$

$$P_B = P_H$$

$$P_A - P_b = P$$

Therefore, a value of P is made independent of $P_H$ and $P_h$.

Further, when the pulmonary arterial pressure is measured instead of, or in addition to, the central venous pressure mentioned in the above embodiment, the catheter is so constructed that a lumen 45 for measuring the pulmonary arterial pressure is extended forwardly from the membrane 44 to a required extent as indicated in dot-and-dash lines in FIG. 3. With this arrangement, by setting the membrane 44 at the reference point, the height variation is similarly compensated for.

As described above, according to the present invention, by positioning at least the distal end of the liquid fill lumen at the pressure reference point, the adjustment of the height of the pressure transducer at the time of starting the measurement is unnecessary, and also the subsequent height variation is compensated for. Therefore, highly precise pressure data can be obtained even when monitoring the pressure for a long period of time, in spite of the movement of the object to be measured. Particularly, data of a pressure having a low absolute value, such as the central venous pressure, can be markedly improved in precision.

What is claimed:

1. An internal pressure measuring device comprising:
    a pressure measuring catheter constituted by a membrane and at least three lumens which are: a pressure measuring lumen having an open distal end; a height-correcting liquid fill lumen having a closed distal end and being suitable to be filled with a liquid; and a height-correcting atmosphere-opening lumen having a closed distal end and having said membrane being disposed between said height-correcting liquid fill lumen and said height-correcting atmosphere-opening lumen, said height-correcting atmosphere-opening lumen having said membrane at a surface thereof in contact with a desired pressure measuring reference point, in an object, said membrane being impermeable to said liquid and permeable to air, a proximal end of said atmosphere-opening lumen being open to the atmosphere at the time of the measurement;
    two pressure measuring transducers, a first transducer connecting to said proximal end of said pressure measuring lumen, and a second transducer connecting to said proximal end of said height-correcting liquid fill lumen, respectively; and
    height-correcting pressure measuring circuit means connecting to said first and second transducers, respectively for electrically adjusting two electric output values corresponding to said pressure values of said first and second transducers, and for outputting a signal to a displaying or recording device.

2. An internal pressure measuring device as claimed in claim 1, wherein said first transducer connecting to said proximal end of said pressure measuring lumen detects an actual pressure value of said object, and said second transducer connecting to said proximal end of said height-correcting liquid fill lumen detects a hydrostatic pressure corresponding to the height of said membrane.

3. An internal pressure measuring device as claimed in Z claim 1, wherein said height-correcting pressure measuring circuit electrically corrects a differential value, defined by subtracting an output value of said second pressure transducer from an output value of said first pressure transducer, to a pressure value measured at said desired pressure measuring reference point in said object, and said height-correcting pressure measuring circuit outputs a corrected value.

4. An internal pressure measuring device comprising:

a pressure measuring catheter constituted by a membrane and at least three lumens which are: a pressure measuring lumen having an open distal end; a height-correcting liquid fill lumen having an closed distal end and being suitable to be filled with a liquid; and a height-correcting atmosphere-opening lumen having a closed distal end and having a membrane being disposed between said height-correcting liquid fill lumen and said height-correcting atmosphere-opening lumen, said height-correcting atmosphere-opening lumen having said membrane at a surface thereof in contact with a desired pressure reference measuring point, in an object, said membrane being impermeable to said liquid and permeable to air, a proximal end of said atmosphere-opening lumen being open to the atmosphere at the time of the measurement;

a height-correcting differential pressure measuring transducer means connected to a proximal end of said pressure measuring lumen and a proximal end of said liquid fill lumen; and a pressure measuring circuit connected to said transducer and outputting a signal to a displaying or recording device.

5. An internal pressure measuring device as claimed in claim 4, wherein said height-correcting differential pressure measuring transducer means is connected to said pressure measuring lumen and said height-correcting liquid fill lumen, respectively, for outputting a pressure value of difference between a pressure value of said pressure measuring lumen and a pressure value of said height-correcting lumen, whereby said height-correcting differential pressure measuring transducer corrects a pressure value to a pressure measured at said desired internal pressure reference point in said object, and said differential pressure measuring circuit transducer outputs a signal.

6. A device as claimed in claim 4, in which said pressure measuring circuit portion comprises:

exciting/receiving circuit means for effecting zero adjustment and temperature compensation of a bridge circuit contained in said differential pressure transducer; and signal processing/output circuit means for detecting a pressure value from an output signal of said exciting/receiving circuit and causing it to be displayed or recorded.

7. A pressure measuring device providing compensation for positional changes of a subject, said device comprising:

a pressure measuring catheter comprising:

a pressure measuring lumen having a first end, and a second end being disposed at a desired internal pressure measuring point;

a height-correcting liquid fill lumen suitable to be filled with a liquid and having a first end, and a second end, said liquid fill lumen having a membrane disposed at a desired pressure reference point in which said membrane is impermeable to said liquid and permeable to air; and an atmosphere opening lumen having a first end open to an atmosphere adjacent said subject, and a second end, having said membrane, such that an atmospheric pressure of said atmosphere can be communicated to said liquid through said membrane;

pressure measuring means including transducer means connected to said first end of said pressure measuring lumen for measuring a pressure value of in said pressure measuring lumen, liquid transducer means connected to said first end of said liquid fill lumen for measuring a liquid pressure value of liquid in said liquid fill lumen, and compensation means for adjusting said pressure value in accordance with said liquid pressure value to compensate for pressure changes induced by a positional change of said subject.

8. A pressure measuring catheter for introducing a pressure measuring error caused by a positional change of a object comprising:

a pressure measuring catheter constituted by a membrane and at least three lumens which are: a pressure measuring lumen having an open distal end for detecting an actual pressure value of an object to be measured; a height-correcting liquid fill lumen having a closed distal end, being suitable to be filled with a liquid for detecting a hydrostatic pressure corresponding to a height of said membrane; and a height-correcting atmosphere-opening lumen having a closed distal end and having said membrane adapted to be in contact with the surface thereof being disposed between aid height-correcting liquid fill lumen and said height-correcting atmosphere-opening lumen, said height-correcting atmosphere-opening lumen having said membrane at a surface thereof in contact with a desired pressure measuring reference point, in said object, said membrane being impermeable to said liquid and permeable to air, a proximal end of said atmosphere-opening lumen being open to the atmosphere at the time of measurement.

* * * * *